US00PP33199P2

(12) United States Plant Patent
Olesen

(10) Patent No.: US PP33,199 P2
(45) Date of Patent: Jun. 29, 2021

(54) MINIATURE ROSE PLANT NAMED 'POULPAH104'

(50) Latin Name: *Rosa hybrida*
Varietal Denomination: Poulpah104

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,997

(22) Filed: Sep. 3, 2020

(51) Int. Cl.
*A01H 5/02* (2018.01)
*A01H 6/74* (2018.01)

(52) U.S. Cl.
USPC ..... Plt./124

(58) Field of Classification Search
USPC ..... Plt./101, 116, 117, 123, 124
See application file for complete search history.

(56) References Cited

PUBLICATIONS

Poulsen Roser. 2020. Citation for 'Poulpah104'. retrieved from the internet at https://www.poulsenroser.dk/en/roses/ShowProduct/62793. 2 pages. (Year: 2020).*

* cited by examiner

*Primary Examiner* — Susan McCormick Ewoldt
*Assistant Examiner* — Karen M Redden

(57) ABSTRACT

A new garden rose plant of the miniature class which has abundant, white flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah104'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpah104', originated as a single seedling from the stated cross.

The new variety may be distinguished from its male pollen parent and female seed parent primarily by the following characteristics. The male pollen parent plant has near white flowers with other intonations of yellow orange flowers while the new variety has pure white flowers. The female seed parent plant has white flowers and grows to a height of about 60 cm, while the new variety has white flowers and grows to a height of 30 cm.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance.

This combination of qualities is not present in previously available commercial cultivars of this type, known to the inventor, and distinguish 'Poulpah104' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpah104' was selected in the spring of 2012 by the inventor as a single plant from the progeny of the aforementioned hybridization.

Asexual reproduction of 'Poulpah104' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpah104' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah104'.

Specifically illustrated in FIG. 1 of the drawings are open flowers at various stages of development, sepals and petals detached showing reproductive flower parts and receptacle.

Figure 1:
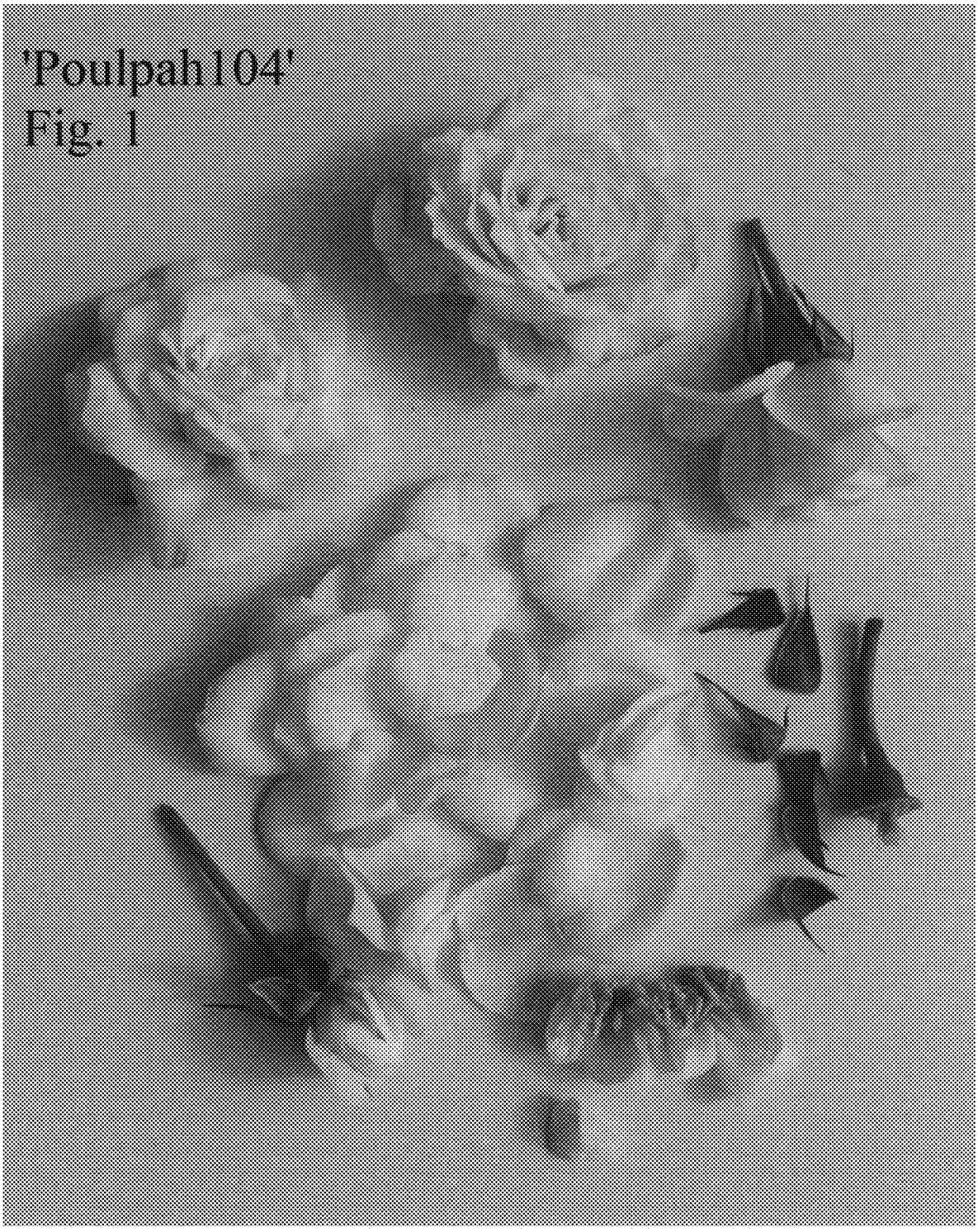
Figure 2:
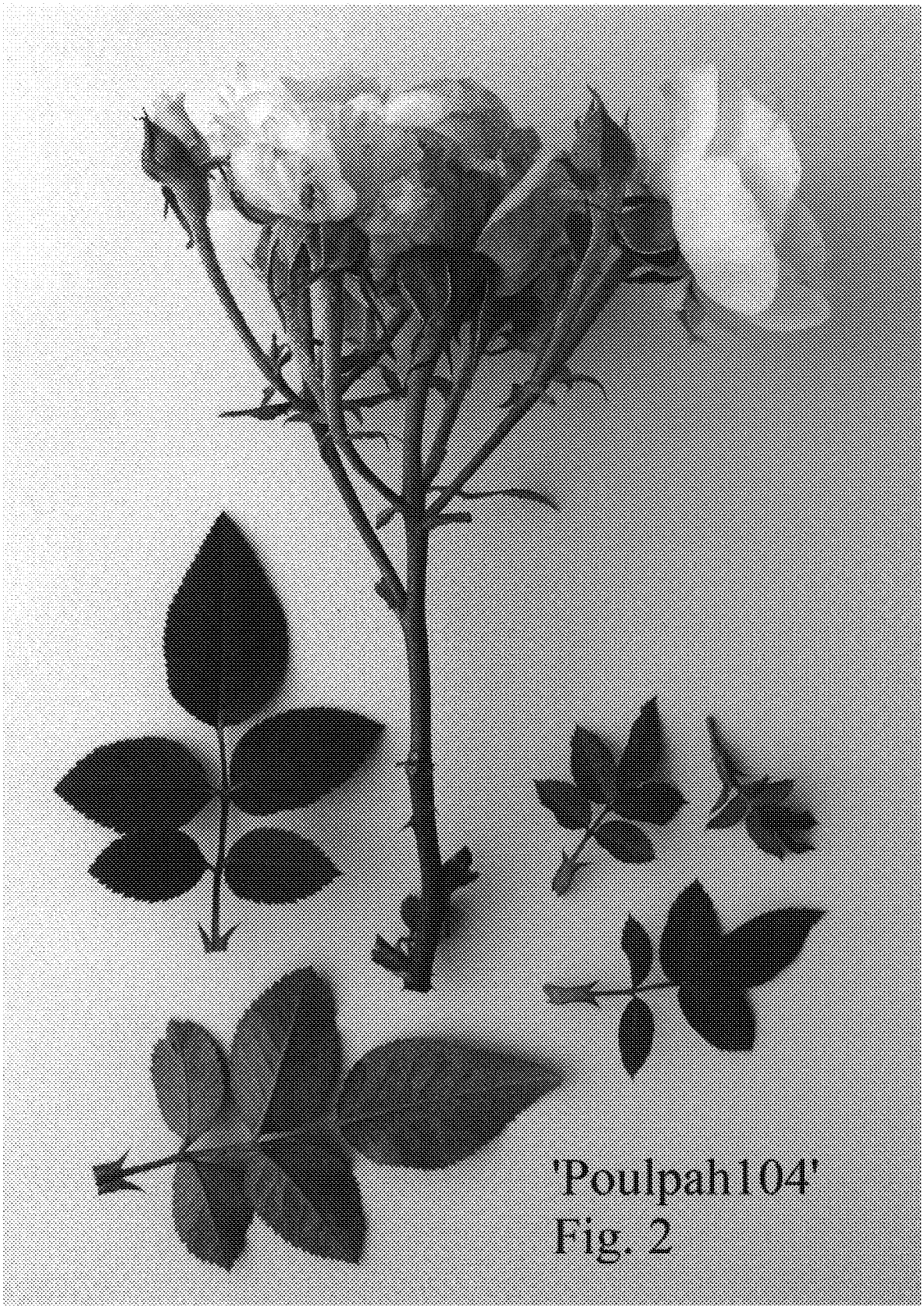

Specifically illustrated in FIG. 2 of the drawings are a cluster of open flowers on a bare stem, mature leaves, and juvenile leaves exhibiting anthocyanin. Plants shown are 1 year of age.

DETAILED DESCRIPTION OF THE VARIETY

The following is a description of 'Poulpah104', as observed in its growth in open air container nursery in Odense Denmark. Observed plants are 12 months old and were grown on their own roots in 23 cm containers. Color references are made using The Royal Horticultural Society (London, England) Colour Chart, 2001, except where common terms of color are used.

For a comparison, several physical characteristics of the rose variety 'Poulpal038', U.S. Plant Pat. No. 25,126 are compared to 'Poulpah104' in Chart 1.

CHART 1

| | 'Poulpah104' | 'Poulpal038' |
|---|---|---|
| Petal Count | 75 to 80 | 26 |
| Flower Diameter | 60 mm | 80 mm |
| General Tonality of Flower Color | White Group 155B | White Group 155B |

FLOWER AND FLOWER BUD

Blooming habit: Continuous.

Flower bud:

*Size*.—Upon opening, 24 mm in length from base of receptacle to end of bud. Bud diameter is 11 mm.

*Bud form*.—Ovoid.

*Bud color*.—As sepals divide petals are Yellow White Group 158C with light intonations of Greyed-Red Group 179B.

*Sepal inner surface*.—Color: Yellow-Green Group 144B with strong intonations of Greyed-Red Group 180A Surface: Lightly pubescent.

*Sepal outer surface*.—Color: Yellow-Green Group 144A with intonations of Greyed-Red Group 180B. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—23 mm long, 6 mm wide.

*Receptacle*.—Texture: Smooth. Size: 8 mm in height, 7 mm wide. Color: Yellow-Green Group 144A with intonations of Greyed-Red Group 180A. Shape: Campanulate.

*Pedicel*.—Surface: Smooth. Length: 30 mm. Diameter: mm on average. Color: Yellow-Green Group 144A with intonations of Greyed-Red Group 180A. Strength: Strong.

*Peduncle*.—Length: 15 to 43 mm. Diameter: About 3 mm. Color: Yellow-Green Group 144A. Texture: Smooth.

Flower bud development: Flower buds are borne in clusters of 3 to 9 flower buds per stem. Development as a panicle.

Flower bloom:

*Fragrance*.—No scent.

*Duration*.—The blooms have a duration on the plant of approximately 18 days. Petals fall cleanly away from plant after flowers have fully matured.

*Size*.—Flower diameter is 60 mm when open. Flower depth is 26 mm.

*Flower shape*.—High centered, very double, with a high pointed center which is tightly closed.

*Shape of flower, side view*.—The upper portion is flat. The lower portion is concave.

Petalage: Under normal conditions, flowers have about 75 to 80 petals.

General tonality of flower: Open flowers are White Group 155B.

Petal color:

*Upon opening, outer petals*.—Upper surface: White Group 155B. Lower surface: White Group 155B. Guard petals are lightly splashed with intonations of Orange-Red Group N34C and streaks of Yellow-Green Group 144C.

*Upon opening, inner petals*.—Upper surface: White Group 155B. Lower surface: White Group 155B.

*Basal petal spots, upon opening*.—Upper surface: Green-Yellow Group 1D. Lower surface: Green-Yellow Group 1D.

*After opening, outer petals*.—Upper surface: White Group 155B. Lower surface: White Group 155B.

*After opening, inner petals*.—Upper surface: White Group 155B. Lower surface: White Group 155B.

*Basal petal spots, after opening*.—Upper surface: Green-Yellow Group 1D. Lower surface: Green-Yellow Group 1D.

Petals:

*Petal reflex*.—Somewhat reflexed.

*Margin*.—Entire and uniform with moderate to strong undulations.

*Shape*.—Broad and elliptic. Apex shape: Rounded. Base shape: Obtuse.

*Size*.—34 mm (l)×34 mm (w).

*Texture*.—Smooth.

*Thickness*.—Average.

Petaloids:

*Size*.—On average 15 mm (l) by 8 mm (w).

*Quantity*.—About 10 to 20.

*Shape*.—Elliptical with an acute base and rounded and or acute apex.

*Color*.—White Group 155B.

Reproductive flower parts:

*Pollen*.—None observed.

*Anthers*.—Size: 2 mm in length. Color: Greyed-Orange 163B. Quantity: 30 on average.

*Filaments*.—Color: Green-Yellow Group 1D. Length: 3 mm.

*Pistils*.—Length: 4 mm. Quantity: 25 on average.

*Stigmas*.—Color: Yellow-Green Group 144D.

*Styles*.—Color: Yellow-Green Group 144D.

*Location of stigmas*.—Inferior in location relative to the length of the filaments and the height of the anthers.

*Hips*.—None Observed.

PLANT

Plant growth: Compact and well branched. Plants are 30 cm in height, and 33 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 9 mm.

*Internodes*.—On mature canes about 26 mm between nodes.

*Surface texture*.—Young wood: Smooth. Older wood: Smooth.

Long prickles:

*Incidence.*—5 prickles per 10 cm of stem.

*Size.*—Average length of prickles on mature stems is 5 mm.

*Shape.*—Upper portion is linear. Lower portion is concave.

*Color.*—Juvenile prickles: Greyed-Red Group 181A. Mature prickles: Greyed-Red Group 181A.

Plant foliage:

*Compound leaf.*—100 mm (l)×78 mm (w).

*Quantity.*—2 leaves per 10 cm of stem on average.

*Leaf bearing angle to the stem.*—45 degrees.

*Color of juvenile foliage.*—Upper side: Yellow-Green Group 144A with intonations of Greyed-Purple Group 183B at margins. Lower side: Yellow-Green Group 144B shaded with Greyed-Purple Group 183B.

*Color of mature foliage.*—Upper side: Yellow-Green Group 147A. Lower side: Yellow-Green Group 147B.

Plant leaves and leaflets:

*Stipules.*—Size: 5 mm long, mm wide. Quantity: 2 per compound leaf. Shape: Linear, slightly broad based with outward extending apices. Margins: Finely serrated. Color: Yellow-Green Group 147A.

*Petiole.*—Length: 13 mm. Diameter: 8 mm. Upper surface color: Yellow-Green Group 144A. Lower surface color: Yellow-Green Group 144A.

*Rachis.*—Length: 30 mm. Upper surface color: Yellow-Green Group 144A. Lower surface color: Yellow-Green Group 144A.

*Leaflet.*—Quantity: Normally 5 leaflets. Margins: Serrated. Size: Terminal leaflets are about 49 mm long, 28 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah104', substantially as illustrated and described herein, due to its abundant white flowers, disease resistance, and extended period of bloom.

* * * * *

'Poulpah104'

'Poulpah104'